United States Patent
Lai et al.

(10) Patent No.: US 7,074,873 B2
(45) Date of Patent: Jul. 11, 2006

(54) HIGH REFRACTIVE INDEX AROMATIC-BASED PREPOLYMERS

(75) Inventors: Yu-Chin Lai, Pittsford, NY (US); Edmond T. Quinn, Rochester, NY (US)

(73) Assignee: Rausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 11/048,501

(22) Filed: Jan. 31, 2005

(65) Prior Publication Data

US 2005/0128425 A1 Jun. 16, 2005

Related U.S. Application Data

(62) Division of application No. 10/889,321, filed on Jul. 12, 2004, now Pat. No. 6,864,342, which is a division of application No. 10/004,484, filed on Nov. 2, 2001, now Pat. No. 6,777,522.

(51) Int. Cl.
*C08G 77/20* (2006.01)
(52) U.S. Cl. .......................... 528/32; 528/43; 528/32; 528/41; 528/85; 528/38; 526/279; 525/288; 523/105; 523/107
(58) Field of Classification Search .............. 528/43, 528/32, 41, 85, 38; 525/288; 523/105, 107; 526/279
See application file for complete search history.

(56) References Cited

U.S. PATENT DOCUMENTS

| | | | |
|---|---|---|---|
| 3,996,187 A | 12/1976 | Travnicek |
| 3,996,189 A | 12/1976 | Travnicek |
| 4,418,165 A | 11/1983 | Polmanteer et al. |
| 4,537,943 A | 8/1985 | Talcott |
| 4,647,282 A | 3/1987 | Fedorov et al. |
| 4,737,558 A | 4/1988 | Falcetta et al. |
| 4,868,251 A | 9/1989 | Reich et al. |
| 4,929,051 A | 5/1990 | Rogler et al. |
| 5,444,106 A | 8/1995 | Zhou et al. |
| 5,512,609 A | 4/1996 | Yang |
| 5,623,029 A | 4/1997 | Yang |
| 5,855,825 A | 1/1999 | Ito |
| 6,039,913 A | 3/2000 | Hirt et al. |

FOREIGN PATENT DOCUMENTS

| | | |
|---|---|---|
| EP | 0335312 A2 | 4/1989 |
| GB | 1604519 A | 9/1981 |
| JP | 63277210 | 11/1988 |
| JP | 02198415 | 8/1990 |

*Primary Examiner*—Kuo-Liang Peng
(74) *Attorney, Agent, or Firm*—Toan P. Vo

(57) ABSTRACT

Relatively high refractive index polymeric compositions and ophthalmic devices such as for example intraocular lenses and corneal inlays made therefrom are described herein. The preferred polymeric compositions are produced through the copolymerization of one or more aromatic-substituted polysiloxane prepolymers with one or more aromatic monomers, alkylated monomers or hydrophilic monomers.

2 Claims, No Drawings

HIGH REFRACTIVE INDEX AROMATIC-BASED PREPOLYMERS

This application is a divisional application of prior application Ser. No. 10/889,321 filed Jul. 12, 2004, now U.S Pat. No. 6,864,342, which is a divisional application of application Ser. No. 10/004,484 filed Nov. 2, 2001, now U.S. Pat. No. 6,777,522 issued Aug. 17, 2004.

FIELD OF THE INVENTION

The present invention relates to prepolymers useful in the manufacture of biocompatible medical devices. More particularly, the present invention relates to aromatic-substituted polysiloxane prepolymers capable of copolymerization with one or more other monomers to form polymeric compositions having desirable physical characteristics and refractive indices for use in the manufacture of ophthalmic implants.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive index materials require a thicker IOL optic portion to achieve a given refractive power. Silicone materials may have higher refractive indices than high-water content hydrogels, but tend to unfold explosively after being placed in the eye in a folded position. Explosive unfolding can potentially damage the corneal endothelium and/or rupture the natural lens capsule and associated zonules. Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings of current polymeric materials available for use in the manufacture of ophthalmic devices, there is a need for stable, biocompatible polymeric materials having desirable physical characteristics and refractive indices.

SUMMARY OF THE INVENTION

Soft, foldable, high refractive index, high elongation, polymeric compositions of the present invention are synthesized through the copolymerization of aromatic-substituted polysiloxane prepolymers with one or more aromatic monomers, alkyl monomers, hydrophilic monomers or a combination thereof. Production processes of the present invention using the subject aromatic-substituted polysiloxane prepolymers, produce materials having desirable physical properties for use in the manufacture of ophthalmic devices. The polymeric compositions of the present invention are transparent and have relatively high strength for durability during surgical manipulation, relatively high elongation and relatively high refractive index. The subject polymeric compositions are particularly well suited for use in the manufacture of ophthalmic devices such as intraocular lens (IOL) implants, contact lenses, keratoprostheses, corneal rings, corneal inlays and the like.

Preferred aromatic-substituted polysiloxane prepolymers for use in the production of the polymeric compositions of present invention have a structure generally represented by Formula 1 below, which may be produced from precursors having a structure generally represented by Formula 2 below:

Formula 1
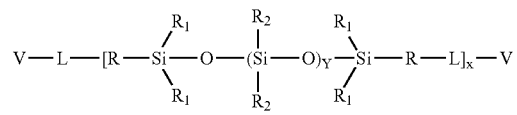

Formula 2
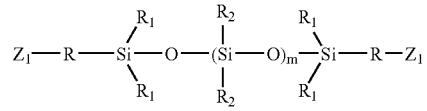

wherein the V groups may be the same or different unsaturated photo or thermal polymerizable substituents of the general structure $R_3CH{=}C(R_4)(CH_2)_p(W)_q(Z)_q(Ar)_qR_5$; the R groups may be the same or different saturated $C_{1-10}$ hydrocarbon substituents; the $R_1$ groups may be the same or different alkyl substituents; the $R_2$ groups may be the same or different alkyl substituents, fluoroalkyl substituents or alkyl-fluoroalkyl substituents with ether linkages therebetween, or the same or different aromatic substituents; the L groups, which may or may not be present in the subject prepolymers, may be the same or different urethane, urea, carbonate or ester linkages; y is a natural number greater than 4 representing the sum of siloxane moieties with randomly differing $R_2$ groups as defined above with a molar ratio of aromatic substituents to alkyl substituents no less than 1:4; x is a natural number such that the prepolymer molecular weight is at least approximately 1000 and refractive index is at least approximately 1.45 or greater; m is a natural number greater than 4 representing the sum of siloxane moieties with randomly differing $R_2$ groups as defined above with a molar ratio of aromatic substituents to alkyl substituents no less than 1:4 such that the prepolymer molecular weight is at least approximately 1000 and refractive index is at least approximately 1.45 or greater; $R_3$ is selected from the group consisting of hydrogen, $C_{1-10}$ alkyl and —CO—U—$R_1$; $R_4$ is selected from the group consisting of hydrogen and methyl; $R_5$ is a $C_{1-10}$ divalent alkylene radical; the W group is selected from the group consisting of —CO— and —OCO—; the Z group is selected from the group consisting of —O— and —NH—; the $Z_1$ groups may be the same or different selected from the group consisting of —OH and —NH$_2$; the Ar groups may be the same or different $C_{6-30}$ aromatic radicals; p is a non-negative integer less than 7; q is either 0 or 1; and U is selected from the group consisting of —O$C_{1-12}$ alkyl radical, —S$C_{1-12}$ alkyl radical and —NH$C_{1-12}$ alkyl radical.

Accordingly, it is an object of the present invention to provide transparent, biocompatible polymeric compositions having desirable physical characteristics and relatively high refractive indices.

Another object of the present invention is to provide polymeric compositions having relatively high refractive indices and good clarity.

Another object of the present invention is to provide polymeric compositions suitable for use in the manufacture of ophthalmic devices.

Another object of the present invention is to provide polymeric compositions suitable for use in the manufacture of intraocular lens implants.

Still another object of the present invention is to provide polymeric compositions that are economical to produce.

These and other objectives and advantages of the present invention, some of which are specifically described and others that are not, will become apparent from the detailed description and claims that follow.

DETAILED DESCRIPTION OF THE INVENTION

The present invention relates to novel aromatic-substituted polysiloxane prepolymers and the use of such prepolymers to produce biocompatible polymeric compositions having desirable physical properties and relatively high refractive indices for use in the manufacture of ophthalmic devices. The aromatic-substituted polysiloxane prepolymers of the present invention are represented generally by Formula 1 below, which are produced from precursors represented generally by Formula 2 below:

Formula 1

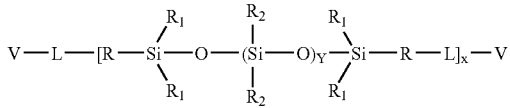

-continued

Formula 2

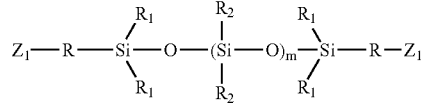

wherein the V groups may be the same or different unsaturated photo or thermal polymerizable substituents of the general structure $R_3CH{=}C(R_4)(CH_2)_p(W)_q(Z)_q(Ar)_qR_5$; the R groups may be the same or different saturated $C_{1-10}$ hydrocarbon substituents such as for example but not limited to methyl, propyl, octyl, trimethylene or tetramethylene but preferably methyl for increased stability; the $R_1$ groups may be the same or different $C_{1-10}$ alkyl substituents such as for example but not limited to methyl, propyl, or octyl but preferably methyl for increased stability; the $R_2$ groups may be the same or different selected from the group consisting of $C_{1-10}$ alkyl substituents such as for example but not limited to methyl, propyl or octyl but preferably methyl for increased stability, $C_{1-10}$ fluoroalkyl substituents such as for example but not limited to fluoromethyl, fluoropropyl or fluorooctyl but preferably fluoromethyl for increased stability, $C_{2-20}$ alkyl-fluoroalkyl substituents, which may or may not have ether linkages between the alkyl and fluoroalkyl substituents, such as for example but not limited to methyl-fluoromethyl, propyl-fluorobutyl or octyl-fluoropentyl but preferably methyl-fluoromethyl for increased stability, and $C_{6-30}$ aromatic substituents such as for example but not limited to phenyl or naphthyl; the L groups, which may or may not be present in the subject prepolymers, may be the same or different urethane, urea, carbonate or ester linkages such as for example but not limited to T, T-$R_6$-T or T-$R_6$-T-$R_7$-T-$R_6$-T; y is a natural number greater than 4 representing the sum of siloxane moieties with randomly differing $R_2$ groups as defined above so as to have a molar ratio of aromatic substituents to alkyl substituents no less than 1:4; x is a natural number such that the prepolymer molecular weight is at least approximately 1000 and refractive index is at least approximately 1.45; m is a natural number greater than 4 representing the sum of siloxane moieties with randomly differing $R_2$ groups as defined above with a molar ratio of aromatic substituents to alkyl substituents no less than 1:4 such that the prepolymer molecular weight is at least approximately 1000 and refractive index is at least approximately 1.45 or greater; $R_3$ is selected from the group consisting of hydrogen, $C_{1-10}$ alkyl such as for example but not limited to methyl, propyl or octyl and —CO—U—$R_1$, but preferably hydrogen; $R_4$ is selected from the group consisting of hydrogen and methyl; $R_5$ is a $C_{1-10}$ divalent alkylene radical such as for example but not limited to methylene or butylene but preferably methylene; the W group is selected from the group consisting of —CO— and —OCO—; the Z group is selected from the group consisting of —O— and —NH—; the $Z_1$ groups may be the same or different selected from the group consisting of —OH and —NH$_2$; the Ar groups may be the same or different $C_{6-30}$ aromatic radicals such as for example but not limited to radicals of benzene, naphthalene or phenanthrene; p is a non-negative integer less than 7; q is either 0 or 1; the T groups may be the same or different selected from the group consisting of —OCONH—, —NHCOO—, —NHCONH—, —OCOO—, —OCO— and —COO—; $R_6$ is a residue of diisocyanate after removing isocyanate groups; $R_7$ is a residue of diol after removing —OH groups; and U is selected from the group consisting of —$OC_{1-12}$ alkyl radical, —$SC_{1-12}$ alkyl radical and —$NHC_{1-12}$ alkyl radical.

Many α,ω-bis-hydroxyalkyl polysiloxanes or α,ω-bis-aminoalkyl polysiloxanes with varying numbers of aromatic units such as those represented by the structure of Formula 2 are useful in making prepolymers of the present invention. The desired number of aromatic units, such as for example phenyl groups, and the desired prepolymer molecular weight can be produced by reacting 1,3-bis-hydroxyalkyl tetramethyldisiloxane or 1,3-bis-aminoalkyl tetramethyldisiloxane with different combinations of dimethyldimethoxysilane, diphenydimethoxysilane and methylphenyldimethoxysilane at molar ratios of choice. Alternatively, the same prepolymers may be prepared by the same method using cyclic siloxanes with different levels of phenyl groups, such as 1,3,5-trimethyl-1,3,5-triphenylcyclotrisiloxane, 1,1,3,3,5,5-hexamethylcyclotrisiloxane, 1,1,3,3,5,5-hexaphenylcyclotrisiloxane, rather than using silanes as mentioned above. Some examples of polysiloxane precursors so prepared, not intended to be limiting, are α,ω-bis-hydroxybutylpoly(methylphenylsiloxane) (HBPMPS) represented by Formula 3 below,

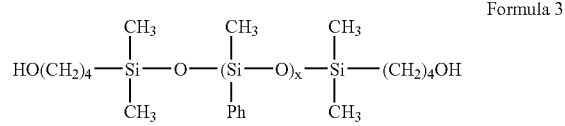

Formula 3 wherein the Ph groups may be the same or different $C_{6-30}$ aromatic substituents such as for example but not limited to phenyl; and x is the same as that defined above for Formula 1; and α,ω-bis-hydroxybutylpoly(methylphenylsiloxane-co-dimethylsiloxane) (HBPMPS-co-DMS) represented by Formula 4 below,

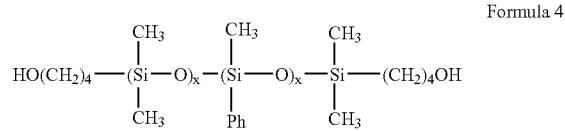

Formula 4 wherein the Ph groups and x are the same as defined above for Formula 3.

Prepolymers of the present invention are also produced using hydroxyalkyl-terminated polysiloxane precursors with aromatic units such as for example HBPMPS of Formula 3 above. One example of such prepolymers, not intended to be limiting, is derived from isophorone diisocyanate and α,ω-bis-hydroxybutylpoly(methylphenylsiloxane) (HBPMPS), end-capped with 2-hydroxyethylmethacylate as represented by Formula 5 below,

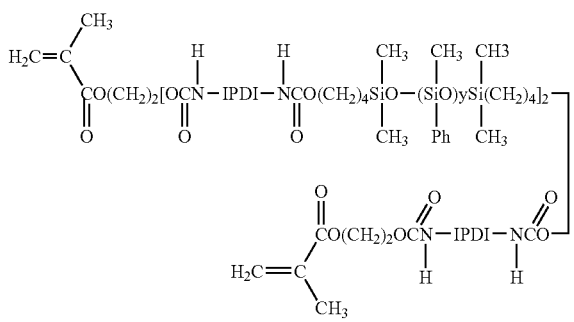

Formula 5 wherein IPDI represents the residue after removing the isocyanate group, and the Ph groups and x are the same as defined above for Formula 3. The prepolymer represented by Formula 5 has three blocks of IPDI and two blocks of HBPMPS repeating units, commonly referred to as a "diblock" prepolymer. Other prepolymers of similar structure can be prepared by the same method using a hydroxyalkyl-terminated polysiloxane with aromatic units having a molecular weight of choice, and a diisocyanate, a diacid chloride or phosgene in a selected molar ratio and end-capped with a hydroxy or amino containing monomer such as for example 2-hydroxyethyl methacrylate.

Soft, foldable, relatively high refractive index of approximately 1.45 or greater, relatively high elongation of approximately 100 percent or greater polymeric compositions of the present invention are synthesized through the copolymerization of one or more of the subject aromatic-substituted polysiloxane prepolymers with one or more aromatic monomers, alkyl monomers, hydrophilic monomers or a combination thereof.

Examples of aromatic monomers useful in the production of polymeric compositions of the present invention include for example but are not limited to acrylate, methacrylate, acrylamide and methacrylamide, each with $C_{6-30}$ aromatic substituents. More specific examples of such aromatic monomers include but are not limited to phenyl acrylate, phenyl(meth)acrylate, phenyl acrylamide, benzyl acrylate, benzyl acrylamide, phenylethylacrylate, phenyl(meth)acrylamide, phenylethyl(meth)acrylate and benzyl(meth)acrylate.

Examples of alkyl monomers useful in the production of polymeric compositions of the present invention include for example but are not limited to $C_{1-20}$ alkyl acrylate, $C_{1-20}$ alkyl methacrylate, $C_{5-20}$ acrylamide and $C_{5-20}$ methacrylamide. More specific examples of such alkyl monomers include for example but are not limited to methyl acrylate, ethyl acrylate, n-propyl acrylate, n-butyl acrylate, n-hexyl acrylate, n-octyl acrylate, 2-ethylhexyl acrylate, n-propyl methacrylate, n-butyl methacrylate, n-hexyl methacrylate, n-octyl methacrylate, 2-ethylhexyl methacrylate and n-octyl acrylamide.

Examples of hydrophilic monomers useful in the production of polymeric compositions of the present invention include for example but are not limited to N,N-dimethyl acrylamide, N-vinylpyrrolidone, 2-hydroxyethyl methacrylate (HEMA), glycerol methacrylate, 2-hydroxyethyl acrylate, acrylamide, n-methyl acrylamide, acrylic acid and (meth)acrylic acid.

The polymeric compositions of the present invention have relatively high refractive indexes of approximately 1.45 or greater, relatively low glass transition temperatures of approximately 30 degrees Celsius or less and relatively high elongation of approximately 100 percent or greater. The polymeric compositions of the present invention with the desirable physical properties noted herein are particularly useful in the manufacture of ophthalmic devices such as but not limited to intraocular lenses (IOLs) and corneal inlays. Examples of polymeric compositions having the above mentioned physical characteristics include those derived from the prepolymer of Formula 5, benzyl acrylate, benzyl methacrylate and dimethylacrylamide (DMA) at different weight ratios. These polymeric materials are either xerogels or hydrogels with up to twenty percent water content by weight per volume (W/V).

IOLs having thin optic portions are critical in enabling a surgeon to minimize surgical incision size. Keeping the surgical incision size to a minimum reduces intraoperative trauma and postoperative complications. A thin IOL optic portion is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The preferred polymeric compositions of the present invention have the flexibility required to allow ophthalmic devices manufactured from the same to be folded or deformed for insertion into an eye through the smallest possible surgical incision, i.e., 3.5 mm or smaller. It is unexpected that the subject polymeric compositions described herein could possess the ideal physical properties disclosed herein. The ideal physical properties of the subject polymeric compositions are unexpected because high refractive index monomers or copolymers typically lend to polymers that have increased crystallinity and decreased clarity, which does not hold true in the case of the subject polymeric compositions.

One or more suitable ultraviolet light absorbers may optionally be used in the manufacture of the subject compositions. Such ultraviolet light absorbers include for example but are not limited to β-(4-benzotriazoyl-3-hydroxyphenoxy)ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl)phenyl]-5-chlorobenzotriazole, 2-[3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacryloyloxypropoxy)phenyl]-5-chlorobenzotriazole wherein β-(4-benzotriazoyl-3-hydroxyphenoxy)ethyl acrylate is the preferred ultraviolet light absorber due to its effectiveness and availability.

The subject compositions having refractive indices of approximately 1.45 or greater and elongation of 100 percent or greater are described in still greater detail in the examples that follow.

EXAMPLE 1

Preparation of Hydroxybutyl-Terminated Copolymer of Dimethylsiloxane and Diphenylsiloxane 1,3-bis(hydroxybutyl)tetramethyl disiloxane (33.70 g, 0.118 mole), dimethyldimethoxysilane (403.18 g, 3.25 moles) and diphenyldimethoxysilane (272.33 g, 1.08 moles) were added in a one-liter round bottom flask. Water (78.29 g) and concentrated hydrochloric acid (11.9 mL) were then slowly added to the flask. The contents of the flask were refluxed for one hour. Methanol (253.3 mL) was distilled from the contents. Water (160 mL) and concentrated hydrochloric acid (130 mL) was added to the flask. The contents of the flask were refluxed for one hour. The contents of the flask were then poured into a separatory funnel. The silicone layer was separated, diluted with 500 mL ether and washed once with 250 mL water, twice with 250 mL 5-percent sodium bicarbonate aqueous solution and twice with 250 mL water. The final organic layer was dried with magnesium sulfate, and then vacuum stripped at 80 degrees Celsius (0.1 mm Hg) to give the crude product. The crude product was then dissolved in 50/50 cyclohexane/methylene chloride and then passed through a silica gel column with the same solvent mixture. The final product was collected in tetrahydrofuran (THF) by passing THF through the silica gel column. The THF fractions were combined, dried and vacuum stripped to give the final product. Size exclusion chromatography (SEC) measurements of the final product indicated less than three percent cyclics and a molecular weight of 2821 by titration.

EXAMPLE 2

Preparation of Methacylate-Capped Prepolymer of Polysiloxane Containing Both Dimethylsiloxane and Diphenylsiloxane Units A 500-mL round bottom flask equipped with reflux condenser and nitrogen blanket was charged with isophorone diisocyanate (5.031 g, 0.0227 mole), the hydroxybutyl-terminated copolymer of dimethylsiloxane and the diphenylsiloxane from Example 1 (51.4465 g, 0.0189 mole), dibutyltin dilaurate (0.1811 g) and methylene chloride (150 mL). The flask contents were refluxed. After about 90 hours of reflux, the isocyanate was found decreased to 16.2 percent (theoretical 16.7 percent) of original. The contents of the flask were allowed to cool to ambient temperature. Hydroxyethyl methacrylate (HEMA) (1.1572 g) and 1,1'-2-bi-naphthol (5.7 mg) were added to the flask and stirred. After seven days, NCO peak disappeared from IR spectrum and the reaction was terminated. The product was obtained at quantitative yield after removing solvent.

EXAMPLE 3

Preparation of Hydroxybutyl-Terminated Polymethylsiloxane with Fifty Percent Phenyl Content 1,3-bis(hydroxybutyl)tetramethyldisiloxane (13.18 g, 0.474 mole) and dimethoxyphenylmethylsilane (238.08 g, 1.306 moles) were added to a one-liter round bottom flask. Water (23.58 g or 1.31 mole) and concentrated hydrochloric acid (4.8 mL) were then slowly added to the flask and the contents refluxed at 70 degrees Celsius for one hour. After refluxing, methanol (69.2 g) was distilled from the flask and 44 mL of water and 44 mL of concentrated hydrochloric acid were added to the reaction mixture. The contents of the flask were then refluxed for 3.5 hours prior to being poured into a separatory funnel. The silicone layer was separated, diluted with 500-mL ether and washed twice with 100-ml water, twice with 100 mL five percent sodium bicarbonate aqueous solution and twice with 250-mL water. The final organic layer was dried with magnesium sulfate, and then vacuum stripped at 80 degrees Celsius (0.1 mm Hg) to give a clear viscous crude product. The crude product was then purified by silica gel column chromatography using the same method as described in Example 1 above. The THF solutions containing product were combined and dried with magnesium sulfate. The solvent was vacuum stripped to give the final product. The molecular weight of the final product as determined by titration was 2,697.

EXAMPLE 4

Preparation of Methacrylate-Capped Prepolymer of Polysiloxane Containing Methylphenyl Siloxane Units The procedure and feed ratio of components used in the present example were the same as those of Example 2 above, except hydroxybutyl terminated polymethylphenylsilloxane was used rather than hydroxybutyl-terminated copolymer of dimethylsiloxane and diphenylsiloxane.

EXAMPLE 5

Preparation of Hydroxybutyl-Terminated Copolymer of Dimethylsiloxane and Diphenylsiloxane with a 27:9 Ratio of Methyl/Phenyl and a Molecular Weight of 4000

The preparation procedure, ingredients and ingredient feed ratio used in the present example were the same as those of Example 1, except preparative SEC was used to purify the crude product. In so doing, the crude product was dissolved in THF (10% w/v) and passed through a preparative SEC unit. The final product, after stripping off all solvent, was over 97 percent pure, with less than 3 percent cyclic impurities. The molecular weight of the final product as determined by titration was 4158.

EXAMPLE 6

Preparation of Methacrylate-Capped Prepolymer of Polysiloxane Containing Both Dimethylsiloxane and Diphenylsiloxane with 25 Percent Phenyl Units The procedure employed in the present example was the same as that described in Example 2 above, except a feed ratio of 4.5:3.5:2.0 on a molar basis for isophorone diisocyanate, silicon of Example 5 and HEMA was used. The isocyanate content before adding the HEMA was 18.5 percent.

EXAMPLE 7

Preparation of Hydroxybutyl-Terminated Copolymer of Dimethylsiloxane and Phenylmethylsiloxane with a 1:3 Ratio of Total Methyl to Phenyl Attached to Silicon and Molecular Weight of 4000

In the present example, the same procedure was employed as that of Example 1, except that the amounts of ingredients used were varied. In the present example, 4-bis(4-hydroxybutyl)tetramethyldisiloxane (19.08 g, 0.0686 mole), dimethoxydimethylsilane (151.67 g, 1.223 mole) and dimethoxyphenylmethylsilane (222.24 g, 1.219 mole) were used. The crude product, after dried, was passed through a preparative SEC column with a 10% w/v THF solution (190 mL inject). The purified product was over 97 percent pure with a molecular weight of 4490.

EXAMPLE 8

Preparation of Methacrylate-Capped Prepolymer of Polysiloxane Containing Both Dimethylsiloxane and Phenylmethylsiloxane Having 25 Percent Total Phenyl Units (2 Blocks of Silicone)

The procedure of the present example was the same as that described in Example 12 below, except a feed ratio of 3:2:2 on a molar basis of isophorone diisocyanate, silicon of Example 7 and HEMA was used.

EXAMPLE 9

Preparation of Methacrylate-Capped Prepolymer of Polysiloxane Containing Both Dimethylsiloxane and Phenylmethylsiloxane Having 25 Percent Total Phenyl Units (1 Block of Silicone)

The procedure of the present example was the same as that described in Example 2 above, except a feed ratio of 2:1:2 on molar basis of isophorone diisocyanate, silicon of Example 7 and HEMA was used.

EXAMPLE 10

Preparation of Methacrylate-Capped Prepolymer of Polysiloxane Containing Both Dimethylsiloxane and Phenylmethylsiloxane Having 25 Percent Total Phenyl Units (3 Blocks of Silicone)

The procedure of the present example was the same as that described in Example 2 above, except a feed ratio of 4:3:2 on molar basis of isophorone diisocyanate, silicon of Example 7 and HEMA was used.

EXAMPLE 11

Preparation of Films by Ultraviolet Light Curing of the Final Product of Example 2 Above (FPEx 2))

The formulations set forth in Chart 1 below also included 0.25 parts benzotriazole methacrylate, 20 parts of hexanol and 1 percent 2,2-dimethoxy-2-phenylacetophenone. The formulations were cured between two silane-treated glass plates under an ultraviolet (UV) light source with an intensity of 300 microwatts for 2 hours. The cured films were then released, extracted in isopropanol for over 4 hours and dried in a vacuum oven at 70 degrees Celsius overnight. The films without extractables were dried in air. All dried films were then placed in a borate buffered saline overnight before characterization. All films had a thickness of 170–200 microns. Tensile tests were performed in borate buffered saline according to ASTM D-1708. The results are set forth in Chart 1 below.

CHART 1

|  | Sample: | | | | | | |
|---|---|---|---|---|---|---|---|
|  | A | B | C | D | E | F | G |
| Formulation: | | | | | | | |
| FPEx2 | 65 | 60 | 60 | 60 | 60 | 55 | 50 |
| BzA | 15 | 15 | 20 | 10 | 25 | 25 | 20 |
| BzMA | 15 | 15 | 10 | 20 | 5 | 5 | 10 |
| DMA | 5 | 10 | 10 | 10 | 10 | 15 | 20 |
| Properties: | | | | | | | |
| % Extractables | 3.4 | 7.5 | 6.9 | 6.9 | 7.1 | 8.0 | 11.1 |
| % Water | 2.6 | 5.7 | 6.9 | 9.6 | 13 | 11.8 | 10.8 |
| Modulus g/mm$^2$ | 1964 | 1791 | 816 | 1980 | 309 | 282 | 132 |
| (Std. Deviation) | (456) | (253) | (56) | (357) | (43) | (43) | (3) |
| % Elongation | 359 | 379 | 389 | 303 | 363 | 360 | 374 |

BzA = benzyl acrylate
BzMA = benzyl methacrylate
DMA = N,N-dimethylacrylamide

EXAMPLE 12

UV Curing of Formulations with a UV Filter

The formulations of the present example also include 0.25 parts benzotriazole methacrylate, 1.0 parts bis-(2,4,6-trimethyl)benzoyl phenyl phosphineoxide and 20 parts hexanol. The formulations were cured with the same light source as that used in Example 11 above, except an UV filter was placed between the light source and the glass plates. All processing conditions were the same as those of Example 11. The results are set forth in Chart 2 below.

CHART 2

|  | Sample: | | | |
|---|---|---|---|---|
|  | H | I | J | K |
| Formulation: | | | | |
| FPEx2 | 100 | 60 | 0 | 0 |
| FPEx4 | 0 | 0 | 65 | 0 |
| FPEx6 | 0 | 0 | 0 | 65 |
| BzA | 0 | 15 | 15 | 15 |
| BzMA | 0 | 15 | 15 | 15 |
| DMA | 0 | 10 | 5 | 5 |
| Properties: | | | | |
| % Extractables | 5.0 | 4.8 | 5.5 | 15.1 |
| % Water | 0.4 | 0 | 1.3 | 0.5 |
| Modulus g/mm$^2$ | 45 | 1209 | 83 | 2176 |
| (Std. Deviation) | (1) | (203) | (4) | (499) |
| % Elongation | 111 | 355 | 313 | 320 |

EXAMPLE 13

Comparison of 2,2-dimethoxy-2-phenylacetophenone and bis(2,4,6-trimethyl)benzoyl Phenyl Phosphineoxide in UV Curing with a UV Filter In the present example, Sample K was used except 2,2-dimethoxy-2-phenylacetophenone was included in the formulation rather than bis(2,4,6-trimethyl)benzoyl phenyl phosphineoxide. After exposure to an UV light source for 2 hours, the formulation remained fluid.

EXAMPLE 14

Comparison of 2-benzyl-2-dimethylamino-1-(morpholinophenyl) -butan-1-one and bis(2,4,6-trimethyl)benzoyl Phenyl Phosphineoxide in UV Curing In the present example, Sample K was used except 2-benzyl-2-dimethylamino-1-(morpholinophenyl)-butan-1-one was included in the formulation rather than bis(2,4,6-trimethyl)benzoyl phenyl phosphineoxide. Films of the so modified Sample K had the following properties: 13.2% extractables; 0.5% water; 309±5% elongation and a modulus of 1841±262 g/mm$^2$.

Results from Examples 13 and 14 indicate that 2,2-dimethoxy-2-phenylacetophenone does not work when the intensity of light in the UV region is curtailed. However, 2-benzyl-2-dimethylamino-1-(morpholinophenyl)-butan-1-one and bis(2,4,6-trimethyl)benzoyl phenyl phosphineoxide proved to work equally well.

EXAMPLE 15

Curing with Blue Light as Compared to an UV Light Source

A quantity of modified Sample K of Example 14 was cured using a blue light source. The films cured using the blue light source had the following properties: modulus g/mm$^2$ 1806±18 and % elongation 321±18. The properties were essentially the same as those of Example 14 above, which indicates that both light sources work equally well.

EXAMPLE 16

Curing Same Formulations but with Different Prepolymers with a Blue Light Source In the present example, the formulations set forth below in Chart 3 were cured using a blue light source as described in Example 15 above. Each formulation also included 0.25 parts benzotriazole methacrylate, 1 percent 2-benzyl-2-dimethylamino-1-(morpholinophenyl)-butan-1-one and 20 parts hexanol. All films were processed according to the same procedure prior to characterization.

CHART 3

| | Sample: | | | | |
|---|---|---|---|---|---|
| | L | M | N | O | P |
| Formulation: | | | | | |
| FPEx2 | 50 | 0 | 0 | 0 | 0 |
| FPEx6 | 0 | 50 | 0 | 0 | 0 |
| FPEx8 | 0 | 0 | 50 | 0 | 0 |
| FPEx9 | 0 | 0 | 0 | 50 | 0 |
| FPEx10 | 0 | 0 | 0 | 0 | 50 |
| BzA | 20 | 20 | 20 | 20 | 20 |
| BzMA | 10 | 10 | 10 | 10 | 10 |
| DMA | 20 | 20 | 20 | 20 | 20 |
| Properties: | | | | | |
| % Extractables | 15.6 | 14.4 | 11.6 | 8.4 | 13.1 |
| % Water | 11.7 | 10.5 | 7.8 | | |
| Modulus, g/mm$^2$ | 94 | 131 | 108 | 279 | 115 |
| (Std. Deviation) | (8) | (41) | (7) | (26) | (9) |
| % Elongation | 438 | 415 | 346 | 222 | 290 |

EXAMPLE 17

Curing Low Water and No Water Formulations Using a Blue Light Source

In the present example, the formulations set forth below in Chart 4 were cured using a blue light source as described in Example 15 above. Each formulation also included 0.25 parts benzotriazole monomer, 1 percent 2-benzyl-2-dimethylamino-1-(morpholinophenyl)-butan-1-one and 20 parts hexanol. All films were processed according to the same procedure prior to characterization.

CHART 4

| | Sample: | | | | | |
|---|---|---|---|---|---|---|
| | Q | R | S | T | U | V |
| Formulation: | | | | | | |
| FPEx2 | 90 | 0 | 0 | 0 | 0 | 0 |
| FPEx4 | 0 | 90 | 0 | 0 | 0 | 0 |
| FPEx6 | 0 | 0 | 90 | 0 | 0 | 0 |
| FPEx8 | 0 | 0 | 0 | 90 | 85 | 85 |
| BzA | 0 | 0 | 0 | 0 | 5 | 0 |
| BzMA | 5 | 5 | 5 | 5 | 5 | 10 |
| DMA | 5 | 5 | 5 | 5 | 5 | 5 |
| Properties: | | | | | | |
| % Extractables | 17.1 | 9.7 | 12.0 | 13.6 | 12.8 | 13.4 |
| % Water | 3.0 | 4.4 | 2.1 | 2.3 | 0.3 | 0 |
| Modulus, g/mm$^2$ | 69 | 81 | 81 | 63 | 62 | 104 |
| (Std. Deviation) | (1) | (4) | (4) | (4) | (15) | (9) |
| % Elongation | 134 | 137 | 132 | 213 | 127 | 203 |

EXAMPLE 18

Cast Molding of Formulations

In the present example, a quantity of Sample K from Example 12 above and a quantity of Sample P from Example 16 above were cast molded between two plastic molds under a UV light source to produce IOLs. The subject IOLs were extracted with isopropanol and proved to have good clarity.

Medical devices produced using the polymeric compositions of the present invention may be manufactured in accordance with methods known to those skilled in the art of the specific ophthalmic device being produced. For example, if an intraocular lens is to be produced, the same may be manufactured by methods known to those skilled in the art of intraocular lens production.

Ophthalmic devices such as but not limited to IOLs and corneal inlays manufactured using the polymeric compositions of the present invention can be of any design capable of being rolled or folded for implantation through a relatively small surgical incision, i.e., 3.5 mm or less. For example, intraocular implants such as IOLs comprise an optic portion and one or more haptic portions. The optic portion reflects light onto the retina and the permanently attached haptic portions hold the optic portion in proper alignment within an eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of the same polymeric composition of the present invention. Alternatively however, the IOL optic portion and haptic portions may be manufactured from different materials and/or different formulations of the polymeric compositions of the present invention, such as described in detail in U.S. Pat. Nos. 5,217,491 and 5,326,506, each incorporated herein in their entirety by reference. Once the material(s) are selected, the same may be cast in molds of the desired shape or cast in the form of rods and lathed or machined into disks. If cast in the form of rods and lathed or machined into disks, the disks may then be lathed or machined at a relatively low temperature below that of the glass transition temperature of the material(s) to produce IOLs. The IOLs whether molded or machined are then cleaned, polished, packaged and sterilized by customary methods known to those skilled in the art.

In addition to IOLs, the polymeric compositions of the present invention are also suitable for use in the production of other ophthalmic devices such as contact lenses, kerato-prostheses, capsular bag extension rings, corneal inlays, corneal rings and like devices.

Ophthalmic devices manufactured using the unique polymeric compositions from the unique prepolymers and prepolymer precursors of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While there is shown and described herein certain prepolymers, polymeric compositions, methods of producing the prepolymers and polymeric compositions and ophthalmic devices made from the subject prepolymers and polymeric compositions in accordance with the present invention. Likewise, it will be manifest to those skilled in the art that various modifications may be made without departing from the spirit and scope of the underlying inventive concept and that the same is not limited to particular structures herein shown and described except insofar as indicated by the scope of the appended claims.

We claim:

1. A method of producing an ophthalmic device using a polymeric composition, said method comprising:
casting said polymeric composition in the form of a rod;
lathing or machining said rod into disks; and
lathing or machining said disks into an ophthalmic device;
wherein said polymeric composition comprises a copolymer of: (a) one or more aromatic monomers, alkyl monomers, hydrophilic monomers, or a combination thereof; and (b) a prepotymer having a formula of

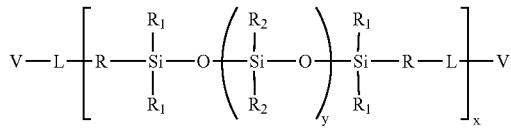

wherein the V groups are the same or different unsaturated photo or thermal polymerizable substituents of the general structure $R_3CH=C(R_4)(CH_2)_p(W)_q(Z)_q(Ar)_qR_5$; the R groups are the same or different saturated $C_{1-10}$ hydrocarbon substltuents; the $R_1$ groups are the same or different $C_{1-10}$ alkyl substituents; the $R_2$ groups are the same or different selected from the group consisting of $C_{1-10}$ alkyl substituents, $C_{1-10}$ fluoroalkyl substituents, $C_{2-20}$ alkyl-fluoroalkyl substituents and $C_{6-30}$ aromatic substituents the L groups, which are absent or present, where present are the same or different urethane, urea, carbonate or ester linkages; y is a natural number greater than 4 representing the sum of siloxane moieties with randomly differing $R_2$ groups as defined above so as to have a molar ratio of aromatic substltuents to alkyl substituents no less than 1:4; x is a natural number such that the prepolymer molecular weight is at least approximately 1000 and refractive index is at least approximately 1.45; $R_3$ is selected from the group consisting of hydrogen, $C_{1-10}$ alkyl and —CO—U; $R_4$ is selected from the group consisting of hydrogen and methyl; $R_5$ is a $C_{1-10}$ divalent alkylene radical; the W group is selected from the group consisting of —CO— and —OCO—; the Z group is selected from the group consisting of —O— and —NH—; the Ar groups are the same or different $C_{6-30}$ aromatic radicals; p is a non-negative integer less than 7; q is either 0 or 1; and U is selected from the group consisting of —$OC_{1-12}$ alkyl radical, —$SC_{1-12}$ alkyl radical and —$NHC_{1-12}$ alkyl radical.

2. A method of producing an ophthalmic device using a polymeric composition, said method comprising:
pouring said polymeric composition prior to curing into a mold;
curing said polymeric composition; and
removing said polymeric composition from said mold following curing thereof;
wherein said polymeric composition comprises a material having a formula of

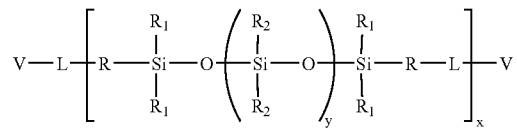

wherein the V groups are the same or different unsaturated photo or thermal polymerizable substituents of the general structure $R_3CH=C(R_4)(CH_2)_p(W)_q(Z)_q(Ar)_qR_5$; the $R_1$ groups are the same or different saturated $C_{1-10}$ a hydrocarbon substituents; the $R_1$ groups are the same or different $C_{1-10}$ alkyl substituents; the $R_2$ groups are the same or different selected from the group consisting of $C_{1-10}$ alkyl substituents, $C_{1-10}$ fluoroalkyl substituents, $C_{2-20}$ alkyl-fluoroalkyl substituents and $C_{6-30}$ aromatic substituents; the L groups, which are absent or present, where present are the same or different urethane, urea, carbonate or ester linkages; y is a natural number greater than 4 representing the sum of siloxane moieties with randomly differing $R_2$ groups as defined above so as to have a molar ratio of aromatic substituents to alkyl substituents no less than 1:4; x is a natural number such that the prepolymer molecular weight is at least approximately 1000 and refractive index is at least approximately 1.45; $R_3$ is selected from the group consisting of hydrogen, $C_{1-10}$ alkyl and —CO—U; $R_4$ is selected from the group consisting of hydrogen and methyl; $R_5$ is a $C_{1-10}$ divalent alkylene radical; the W group is selected from the group consisting of —CO— and —OCO—; the Z group is selected from the group consisting of —O— and —NH—; the Ar groups are the same or different $C_{6-30}$ aromatic radicals; p is a non-negative integer less than 7; q is either 0 or 1; and U is selected from the group consisting of —$OC_{1-12}$ alkyl radical, —$SC_{1-12}$ alkyl radical and —$NHC_{1-12}$ alkyl radical.

* * * * *